United States Patent [19]

Ohashi et al.

[11] Patent Number: 5,565,329

[45] Date of Patent: Oct. 15, 1996

[54] METHOD FOR DETERMINING HISTAMINE BY MEASURING DISSOLVED OXYGEN

[75] Inventors: Minoru Ohashi, Tokyo; Osamu Adachi, Yamaguchi, both of Japan

[73] Assignee: Kikkoman Corporation, Chiba-ken, Japan

[21] Appl. No.: 437,778

[22] Filed: May 9, 1995

Related U.S. Application Data

[63] Continuation of Ser. No. 31,376, Mar. 9, 1993, abandoned.

[30] Foreign Application Priority Data

Mar. 18, 1992 [JP] Japan .................................. 4-108336

[51] Int. Cl.$^6$ .............................. C12Q 1/26; C12N 9/00; A23L 1/31
[52] U.S. Cl. .................................. 435/25; 435/4; 435/27; 435/28; 435/183; 435/191; 435/192; 435/225; 435/287.5; 435/814; 435/817; 435/917; 435/287.1; 426/52; 426/56
[58] Field of Search .................................. 435/25, 4, 27, 435/28, 183, 191, 192, 225, 291, 814, 817, 917; 426/52, 56

[56] References Cited

U.S. PATENT DOCUMENTS

| | | | |
|---|---|---|---|
| 4,045,296 | 8/1977 | Sternberg | 435/807 |
| 4,650,752 | 3/1987 | Ohashi et al. | 435/15 |
| 4,725,540 | 2/1988 | Underberg et al. | 435/42 |

OTHER PUBLICATIONS

Karube et al., *Enzyme Microbiol Technol.*, vol. 2, pp. 117–120, Apr. 1980.

Yamada et al., *Agr. Biol. Chem.*, vol. 29, No. 7, pp. 649–654, 1965.

Yamanaka et al., *Journal Food Hygenic*, vol. 30, No. 5, pp. 396–399, Oct. 1989.

Stoner, *Chemical Abtracts*, vol. 104, p. 232, Ref.#2538W, 1986 (Agents Actions 1985, 17(1) 5–9).

Yauragouri et al., *Chemical Abstracts*, vol. 107, p. 283, Ref#171090m, 1987 (Chem. Pharm. Bull. 1987, 35(7), 3037–40).

Yamanaka et al., "Simultaneous Determination of Polyamines in Red Meat Fishes by High Peformance Liquid Chromatography and Evaluation of Freshness", Journal Food Hygienic, Oct. 1989, vol. 30, No. 5, pp. 396–399.

Yamanaka et al., "Polyamines as Potential Indexes for Decomposition of Pork, Beef and Chicken", Journal Food Hygienic, Oct. 1989, vol. 30, No. 5, p. 401.

Yamada et al., "Amine Oxidases of Microorganisms Part II. Purification and Crystallization of Amine Oxidase", Agr. Biol. Chem., 1965, vol. 29, No. 7, pp. 649–654.

Yamada et al., "Amine Oxidases of Microorganisms Part I. Formation of Amine Oxidase by Fungi", Arg. Biol. Chem., 1965, vol. 29, No. 2, pp. 117–123.

Staruszkiewicz Jr. et al., "Decomposition In Foods Fluorometric Determination of Histamine in Tuna: Development of Method", Journal Of The AOAC, 1977, vol. 60, No. 5, pp. 1125–1130.

Staruszkiewicz Jr. et al., "Fluorometric Detemination of Histamine in Tuna: Collaborative Study", Journal Of The AOAC, 1977, vol. 60, No. 5, pp. 1131–1136.

"Histamine in Seafood Fluorometric Method", AOAC Official Methods of Analysis, 1990, pp. 876–877.

Karube et al., "Monoamine Oxidase Electrode in Freshness Testing of Meat", Enzyme Microb. Technol., Apr. 1980, vol. 2, pp. 117–120.

Lerke et al., "A Rapid Fluorometric Method For The Determination Of Histamine In Canned Tuna", Journal Of Foods Science, 1976, vol. 41, pp. 1282–1284.

*Primary Examiner*—Elizabeth C. Weimar
*Assistant Examiner*—Abdel A. Mohamed
*Attorney, Agent, or Firm*—Foley & Lardner

[57] ABSTRACT

The present invention relates to a method of determining histamine content as a freshness index of food. An examination liquid is injected in a reaction cell, an amount of dissolved oxygen (DO) is recorded through an oxygen sensor and an amplifier in the recorder. Then, an enzymatic reagent having histamine oxidase activity is injected in the reaction cell, a decrease in the dissolved oxygen is recorded in the recorder, and the histamine concentration is determined on the basis of the decrease by a micro computer.

9 Claims, 6 Drawing Sheets

Fig. 6 point a, a' : Hm
point b : Cad
point c : Put

METHOD FOR DETERMINING HISTAMINE BY MEASURING DISSOLVED OXYGEN

This application is a continuation of application Ser. No. 08/031,376, filed Mar. 9, 1993, now abandoned.

BACKGROUND OF THE INVENTION

1. Field of the Invention

The present invention relates to various fields such as the food processing, marine product, food hygiene, medical care and analytical instrument industries or the like.

2. Description of the Related Art

Histamine (Hm) is one of amines. It has a molecular formula of $C_5H_9N_3$, a molecular number of 111, and a chemical structure represented by the formula (1). Histamine is not present in fresh fish, mollusk and meat. However, when they are contaminated by a microbe which has a strong histidine decarboxylase activity, histamine is produced as a toxic substance from histidine of a free amino acid in a protein organization due to a decarboxylating reaction shown in the formula (1).

(1)

When a food containing a large amount of histamine is ingested, an allergy-like poisoning is caused. The symptom of flushing appears on a face or the like from several minutes to several hours after meal, and followed by itching, urticaria, and eczema. In the worst case, the urticaria spreads all over the body and causes bronchitis and hypotension, thereby sometimes inviting a death.

It is generally said that bluefishes of red meat such as mackerel, skipjack, tuna, sardine, horse mackerel, etc. and beef or the like contain a large amount of free histidine, and easily cause a histamine poisoning. However, histamine poisonings caused by other protein food are also reported [D. E. Kramer et al. Seafood Quality Determination, 235–244, Elsevier Science Publishers B. V. Amsterdam (1986)].

It is pointed out that many histamine poisoning incidents occur in a region like Japan where a large amount of fish and mollusk are eaten.

In order to prevent the poisoning incidents, it is required to give care in particular to freshness and quality of fish and mollusk. Even if any abnormality can not be confirmed from a functional finding of fish and mollusk, 100 to 500 mg/100 g of an extremely large amount of histamine is sometimes contained therein. The control therefor is very difficult.

In Japan, a K value of decomposition rate of nucleotide is widely used as a freshness index of fish and mollusk, while the United States Food and Drug Administration (F.D.A.) has adopted histamine restriction (U.S. Federal Register in Sep. 4, 1982). If 10 to 20 mg histamine/100 g of meat in canned tuna is found, some action is officially taken. If not less than 50 mg of histamine is found, it is regarded as toxic for health. Thus, AOAC official method of analysis based on a fluorescent measurement has been established [W. F. Staruszkiewicz, et al., J. Assoc. Off. Anal. Chem., 60, 1125–1130 (1977)].

This fluorometric analysis is recognized as the most suitable method for determination of histamine contained in fish and mollusk. Similar methods are also employed in Europe. These analytical methods all use o-phthalaldehyde as a fluorescent reagent which yields a fluorophore by a condensation reaction with histamine. The intensity of the fluorophore is measured by a photofluorometer. However, before the condensation reaction, it is required to clean a sample by removing inhibitory constituents to the reaction. Therefore, means and time required for carrying out an anion exchange resin column treatment or a cation exchange resin column treatment or the like are inevitable.

Many studies of determination of histamine by a chromatography have been made. A thin-layer chromatography and a paper chromatography are relatively inexpensive measuring device and can measure simultaneously many samples, while an accuracy of determination is not sufficient. Further, it is pointed out that since nonvolatile amines like histamine can not be directly determined by a gas chromatography, there is an inconvenience of converting it into heptafluorobutyl derivatives before determination thereof.

In Japan, the determination by a high performance liquid chromatography (HPLC) is recognized as the most suitable method as described in Standard Methods of Analysis for Hygienic Chemists. Recently Yamanaka et al. have made a study of determination of histamine in red meat fish by the method of HPLC [J. Food Hygienic Soc. Jap. 30, 397–400 (1989)]. The result was scientifically excellent, since seven species of amines yielded simultaneously were successfully separated for determination with high sensitivity. However, this HPLC method requires a high order device and it takes one hour to operate the chromatography. These are problems for wide use of this method.

SUMMARY OF THE INVENTION

As is clear from the description hereinbefore, a rapid, simple, accurate and economical determining method for histamine which responds to the needs in food processing factories, the food hygiene supervisory organization, and a clinical examination laboratory or the like has not yet been developed. Therefore, in view of the necessity for such a determining method, an earnest study has been made and has attained the present invention.

It is therefore an object of the present invention to provide, a simple, rapid and accurate determining method of histamine which is highly needed in the above mentioned various industrial fields.

Another object of the invention is to ensure a safety of food.

Still another object of the invention is to contribute to development of food hygiene technique, and medical technique by applying the present invention to food hygiene examination, clinical examination or the like.

The present invention is completed by applying an enzymatic reagent having a specifically strong histamine oxidase activity derived from a microorganism to a reaction analyzer provided with an electrochemical sensor.

In a conventional determination method of histamine, it was required to separate previously the determination inhibitory constituent and histamine from a sample solution as described above. In contrast, the essential feature of the present invention is as below: an enzymatic reagent having specifically strong oxidase activity to the histamine is used. An uptaken amount of dissolved oxygen (hereinafter referred to with DO) yielded by adding the enzymatic reagent into a sample solution is measured and recorded by an oxygen sensor (hereinafter referred to with DO sensor) in real time. It is an important characteristic that this method requires no separating operation of histamine before the assay. It should be noted that the method according to the present invention can immediately determine a content of histamine by using an air saturated liquid as a reference solution without using a standard histamine solution.

The method of the present invention will be described hereinafter step by step.

When a determination of histamine in fish and mollusk, and meat is carried out, at first histamine should be extracted from the sample.

For this purpose, perchloric acid (PCA), trichloroacetic acid (TCA), heated and neutral phosphate buffer solution or the like which are employed conventionally in a K value determination are also employed.

An enzymatic reagent required for the present invention is prepared according to the search report [H. YAMADA, O. Adachi and K. Ogata, Agr. Biol. Chem., Vol. 29, No. 7, p. 649 to 654 (1963) published in Japan] as below: an enzyme is extracted from a cell mass belonging to *Aspergillus niger* cultured in a culture medium including amine as a nitrogen source. The enzyme is purified by using an ammonium sulfate salting-out technique, and DEAE-cellulose column chromatography or the like. The purified enzyme is further purified by an affinity chromatography or a hydroxyapatite column chromatography to obtain a high purity, and is concentrated by a dialysis tube, using glycerin. Thus obtained highly purified enzyme is suspended in about 2M ammonium sulfate aqueous solution to be the enzymatic reagent. The enzyme used in the present invention is Cu-containing amine oxidase (enzyme number EC 1.4.3.6). The activity of the enzyme measured by Tabor method is $10^5$ Unit/ml. The enzymatic reagent used in the present invention is inactivated rapidly at a temperature of not less than 40° C. So, if the enzymatic reagent is stored in a refrigerator at a temperature of about 5° C. so as not to be frozen, it can be used for a long time.

About 10 μl of the enzymatic reagent is added to about 1 ml of the sample solution, and they are mixed together well. Then, the reaction of the equation (2) progresses rapidly under the reacting conditions which will be described hereinafter, and DO of the reactant is taken up.

Figure 1:
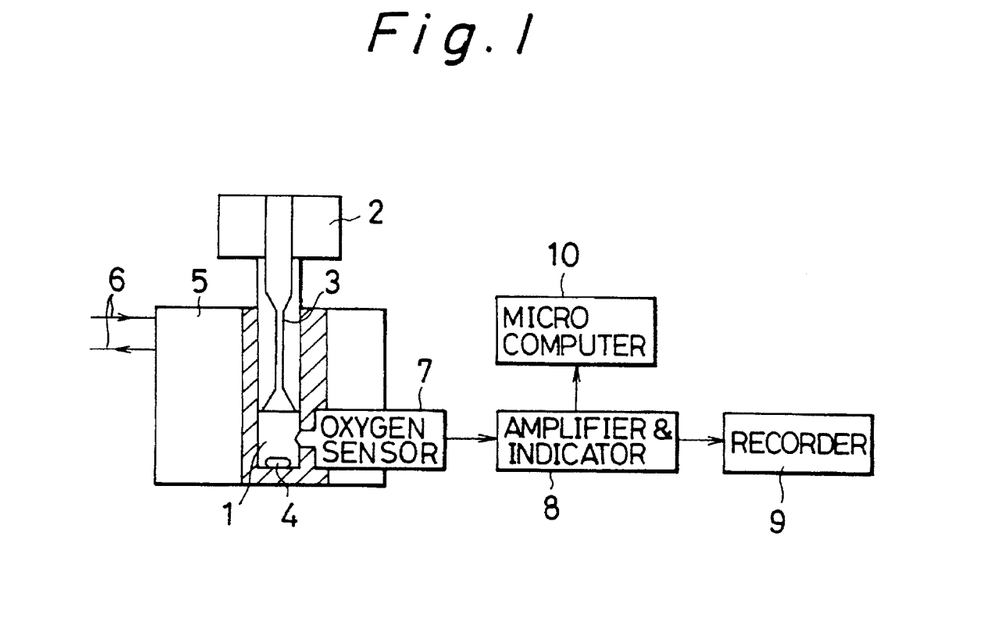
FIG. 1 is a schematic diagram of a dissolved oxygen analyzer most preferable for working the present invention.

An analyzer used for the above reaction is not particularly limited. However, the dissolved oxygen analyzer disclosed in U.S. Pat. No. 4,650,752 (Mar 17, 1987) by the same inventors of the present invention, is the most suitable. FIG. 1 is a schematic diagram of the analyzer. Reference numeral 1 denotes a reaction cell, 2 denotes a reaction cell cap, 3 denotes an injection port for a reagent and a sample, 4 denotes a stirrer, 5 denotes a jacket, 6 denotes an isothermal water, 7 denotes an oxygen sensor, 8 denotes an amplifier/indicator, 9 denotes a recorder, and 10 denotes a microcomputer.

Further objects and advantages of the present invention will be apparent from the following description of the preferred embodiments of the invention as illustrated in the accompanying drawings.

DESCRIPTION OF THE PREFERRED EMBODIMENTS

The method according to the present invention by using an analyzer will be described hereinafter.

I. Preparation of Reagent (1) Histamine standard solution:

Histamine-dihydrochrolide 166 mg made by Wako Chemicals, reagent grade (guaranteed purity 97%) (Lot No. 081-03551) which is dried under vacuum at a room temperature for three hours is exactly measured. It is dissolved in distilled water, and injected into a volumetric flask of 100 ml. Water is added upto a standard line in the volumetric flask. Thus, 9.02 mM of standard solution is prepared. The standard solution is stored in a refrigerator at a temperature of 5° C. for use.

(2) Phosphate buffer solution (0.1M, pH8.0) hereinafter referred to as P.B.) is prepared by using $KH_2PO_4$ and $Na_2HPO_4$ (both are Wako Chemicals, reagent grade). P.B is injected into a BOD bottle placed in an isothermal water tank at a temperature of 37° C. attached in a freshness analyzer. P.B. is aerated previously by air pump for ten to twenty minutes to be saturated with oxygen. If necessary, 2 to 3 mM of sodium azide is added thereto to prevent a contamination caused by catalase.

(3) An enzymatic reagent in a small vial is taken out from the refrigerator and is put into an ice bath to be used while cooling it.

II. Setting up of Analyzer

A temperature of the reaction cell of the dissolved oxygen analyzer (FIG. 1) is set at 37° C. by an exterior isothermal water tank of circulation type. A chart speed of the attached recorder 9 is set to 10 mm/min. A full scale output and a span thereof are 10 mV, and 100 mm, respectively.

An actual value of a volume of the reaction cell of the used freshness analyzer is V=1150 μl. A saturated dissolved oxygen concentration of 0.1M. P.B. at a temperature of 37° C. is decided as 0.214 mM, according to official oxygen solubility table.

III. Determining Operations

The determining operations are carried out by the steps (a) to (j). They are very simple and completed in a short time for several minutes.

(a) The cap 2 is separated and about 1.2 ml of P.B. is injected in the reaction cell 1.
(b) The cap 2 is attached quietly to close thoroughly the reaction cell 1 (confirming no bubble).
(c) A liquid agitation by a magnetic stirrer 4 is commenced.
(d) A histamine standard solution (20 μl) (or sample solution) is injected through the injecting port 3.
(e) A digital display of the freshness analyzer is adjusted to 100 (located at 80 mm of a recorder pen).
(f) A DO recording is commenced ($d_0$).
(g) An enzymatic solution (15 μl) is injected through the injection port 3 airtightly.
(h) A DO recording is continued (about two minutes) until DO decrease stops.
(i) A width of a decrease (d) in DO output is measured.
(j) The reaction cell 1 is cleansed.

Figure 2:
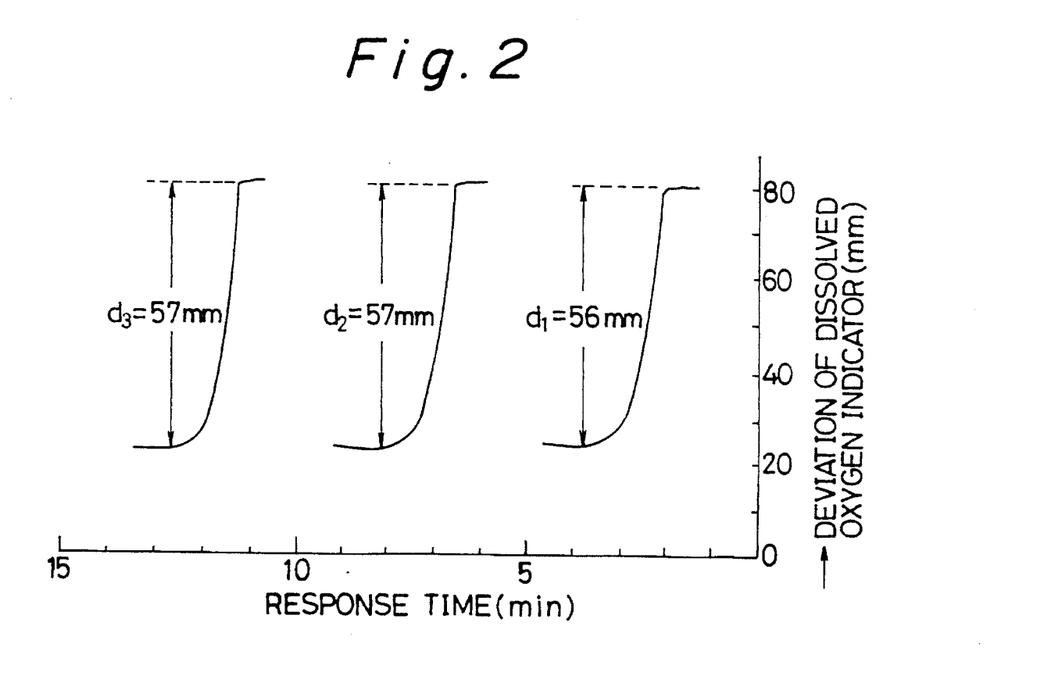
FIG. 2 is a response curve diagram of the dissolved oxygen (DO) in the present invention.

It should be noted that the aforementioned operations are repeated two or three times for a confirmation of reproductivity (See FIG. 2).

IV. Stoichiometrical relationship between histamine and DO uptake (See FIG. 2)

A sensor output responsive to saturated dissolved oxygen concentration $Co_2$ at the reaction starting moment corresponds to 80 mm($d_0$) on a recording paper.

A reproductivity measurement value of decrease value (d) of DO: $d_1$=56 mm, $d_2$=57 mm, $d_3$=57 mm, average value d=56.67 mm, n=3, standard deviation $\sigma_{n-1}$=0.577, and coefficient of variance (c.v.)=0.98%

By the proportional relationship between the output of the DO sensor and the oxygen concentration, the DO uptaken amount is calculated by using the equation (3).

$$DO \text{ uptake} = Co_2 \times \frac{d}{d_0} = 0.214 \text{ (mM)} \times \frac{d}{d_0} = \qquad (3)$$

$$0.214 \text{ (mM)} \times \frac{56.67}{80} = 0.152 \text{ mM}$$

Concentration of histamine in the reaction cell is calculated by the following equation (4).

$$C_{Hm} = \text{(standard solution concentration)} \times \qquad (4)$$

$$\frac{\text{injected volume } (V_s)}{\text{reaction cell volume } (V)} = 9.02 \text{ (mM)} \times \frac{20}{1150} = 0.157 \text{ (mM)}$$

The purity of the reagent is 97%, therefore 0.157×0.97= 0.152 mM. It is confirmed by referring to eq. (3) and (4) that a molar ratio of the oxygen uptake calculated from the DO decrease to reacting histamine is 1:1.

Thus, the oxygen uptake is obtained by aforementioned operations according to the present invention, so that histamine can be determined immediately, on the basis of an equimolar relationship between histamine and oxygen uptake. Differently from the AOAC method and other general determination methods, labors required for preparing a calibration curve from a standard solution or the like becomes unnecessary. The above calculation can be automatically executed and can be printed out by a computer.

Figure 3:
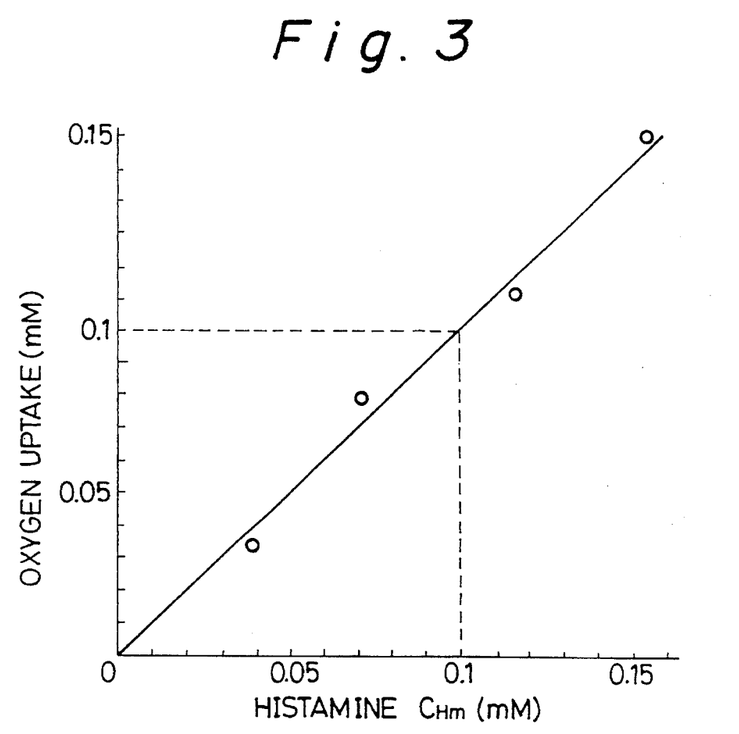
FIG. 3 is a graph showing a proportional molar relationship of 1:1 between histamine concentration and oxygen uptake amount.
Figure 4:
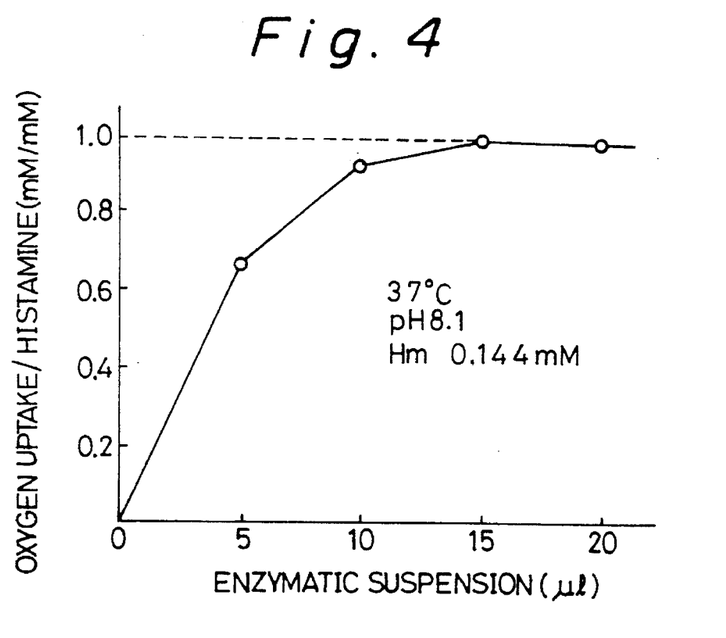
FIG. 4 is a graph showing a relationship between a used amount of enzymatic suspension and oxygen uptake.

As shown in FIG. 3, the stoichiometrical relationship between histamine and oxygen can be measured in a concentration range from 0.002 to 0.2 mM. FIG. 4 shows that 15 μl of enzyme is optimum to be added in the reaction cell of about 1 ml.

V. PH effect for DO uptake reaction

Figure 5:
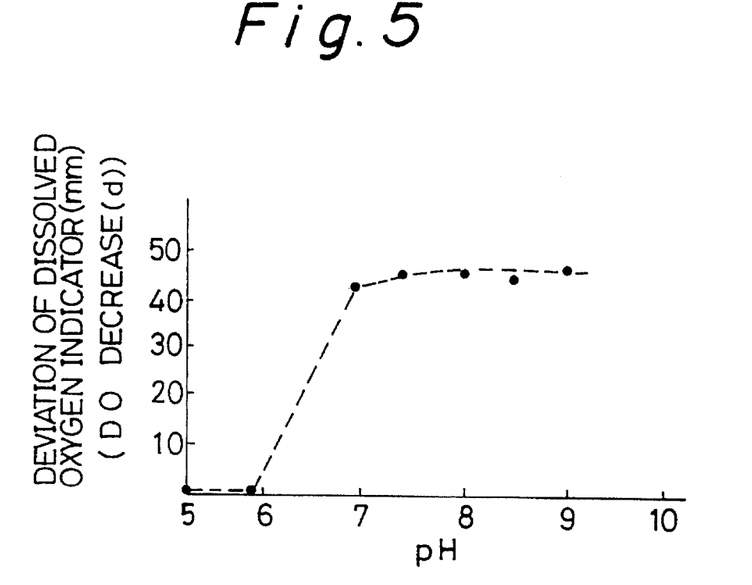
FIG. 5 is a graph showing a range of optimum pH of an enzymatic reaction according to the present invention by a decreased amount of DO.

FIG. 5 shows a pH effect on DO uptake reaction. The activity of the enzyme used in the present invention was inhibited at not grater than pH 6. As aforementioned, stoichiometrical uptake of 1 mol oxygen for 1 mol histamine could be confirmed in the range of pH 7 to 11. The above experiment was carried out by using 0.1M P.B. and a histamine standard solution at 37° C.

VI. Selective Reactivity of Enzyme to Histamine (See FIG. 6)

Figure 6:
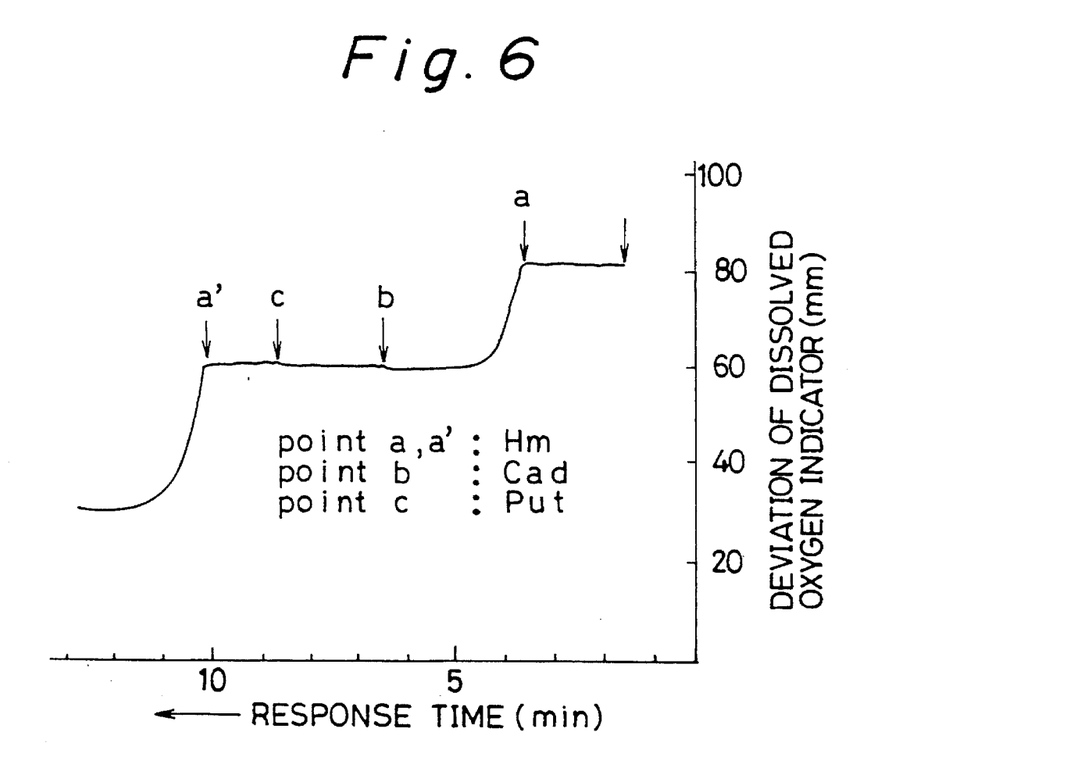
FIG. 6 is a graph showing a selective response of enzyme used in the present invention to histamine in the presence of putrefactive amines.

A histamine standard solution (10 μl) was injected by the aforementioned determining operations at the point "a" of DO curve. An enzymatic activity was confirmed from a decrease in DO at the point "a" of DO curve. Then, 6.9 mM of cadaverine aqueous solution (hereinafter referred to as Cad.) and 8.7 mM of putrescine aqueous solution (hereinafter referred to as Put.) were injected, respectively (20 μl). As clearly seen at the points "b" and "c" of DO curve, no decrease in DO caused by addition of these reagent could be confirmed. Therefore, this shows that the enzyme used in the present invention has no reactivity to Cad and Put. After that, histamine was added again at point "a'", then an oxygen uptake reaction proceeded rapidly. This shows that the enzyme used in the present invention has a characteristic of reacting selectively only to histamine in a mixed solution with histamine, Cad, and Put.

Cad and Put are amines which are produced simultaneously with histamine when fish meat is decomposed. In a conventional histamine analysis, these Cad and Put are required to be eliminated by some method before analysis. However, in the method of the present invention, troublesome and time consuming separating operation becomes unnecessary due to the excellent reactivity characteristic of the enzyme.

VII. Control of Temperature

The method of the present invention can be worked in an optional room temperature at which an enzyme can act fully. Therefore, it is useful to be able to work the method of the present invention without any isothermal tank. However, the saturated dissolved oxygen concentration of the reagent solution on the basis of which concentration of histamine is obtained is calculated taking into account variation of the concentration thereof depending on a temperature as shown in Table 1. The numerical value shown in Table 1 was obtained by using official oxygen solubility data of air saturated pure water. The values for 0.1M P.B. employed in the present invention is close to these numerical values. So, practically there is no problem.

Table 1 below shows dissolved oxygen concentration of air saturated pure water ($C_{O_2}$).

TABLE 1

| temperature (°C.) | 25 | 30 | 35 | 37 | 40 |
|---|---|---|---|---|---|
| $C_{O_2}$ (mM) | 0.253 | 0.235 | 0.220 | 0.214 | 0.206 |

The numerical values of Table 1 were obtained under the condition of an atmospheric pressure of 760 mmHg. If the effect of atmospheric pressure is corrected, accuracy is improved. As a standard reaction temperature, 37° C. is recommended. Although not shown in Table 1, there is a risk of inactivating the enzyme at a reaction temperature not less than 40° C. The temperature should not therefore exceed 40° C.

When the enzymatic reagent is not used, it is stored in refrigerator at a temperature between 0° and 5° C.

VIII. Influence of Catalase Contamination and Its Prevention

As clearly explained hereinbefore, the histamine determination can be very easily carried out. However, it should be careful that the determination is occasionally influenced by catalase contamination.

Figure 7:
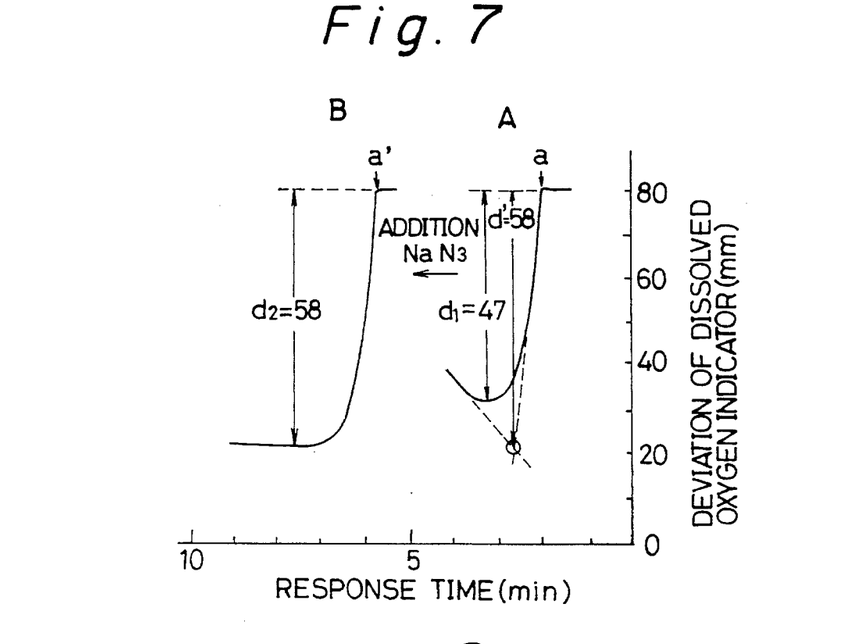
FIG. 7 is an explanatory graph showing a graphical correction of DO response error by contaminating catalase and a preventing effect of an increase of DO caused by adding a sodium azide.

FIG. 7 shows its concrete example and prevention. Under a standard reacting condition at a temperature of 37° C., pH 8.0, 20 μl of 9.02 mM histamine dihydrochloride was injected, and 15 μl of enzymatic reagent was added thereto to react to histamine. A slightly upward tendency of DO was observed at final stage of the reaction. At that moment, the decrease $d_1$ of the output of DO was 47.00 mm, and was much smaller than d=56.67 mm obtained at the above item III. This phenomenon was caused because catalase is mixed in the reagent solution from some source, and hydrogen peroxide produced by the reaction shown in the formula (2) was decomposed by catalase as the following formula (3) to yield oxygen. This is a cause of underestimating a concentration of histamine.

$$2H_2O_2 \xrightarrow{\text{catalase}} 2H_2O + O_2 \quad (3)$$

In order to correct graphically the above estimation error, tangents touching a downward part and upward part of DO response curve respectively are drawn as dot lines in FIG. 7, and d' was obtained from an intersection formed by the two tangents. A relatively exact value can be obtained by using this extrapolating method. Here, a corrected value d' was 58 mm. This value was coincident with a theoretical value.

A drastic method for prevention from the influence of catalase is to add into the reaction mixture an appropriate amount of sodium azide which is a chemical reagent having a remarkable inhibitory effect of a catalase activity. An upward phenomenon of DO response curve B was completely prevented by adding 20 μl of 100 mM sodium azide aqueous solution into the reaction mixture (concentration of 2 mM in the reactant solution). As the result thereof $d_2$=58 mm was coincident with a theoretical value.

Catalase is an enzyme which is widely distributed in the natural world, and is easy to contaminate the reactant. For the safety's sake, it is recommended to inject previously 2 to 5 mM of sodium azide into the P.B. solution. The injection of sodium azide is useful. However, too much injection should be avoided since there is a risk that activity of histamine oxidase is inhibited.

Differently from the aforementioned idea, there is also another preventing method by using efficiently the function of catalase for the determining method of the present invention. This is carried out by making use of sufficiently large amount of catalase present in a reaction system.

Figure 8:
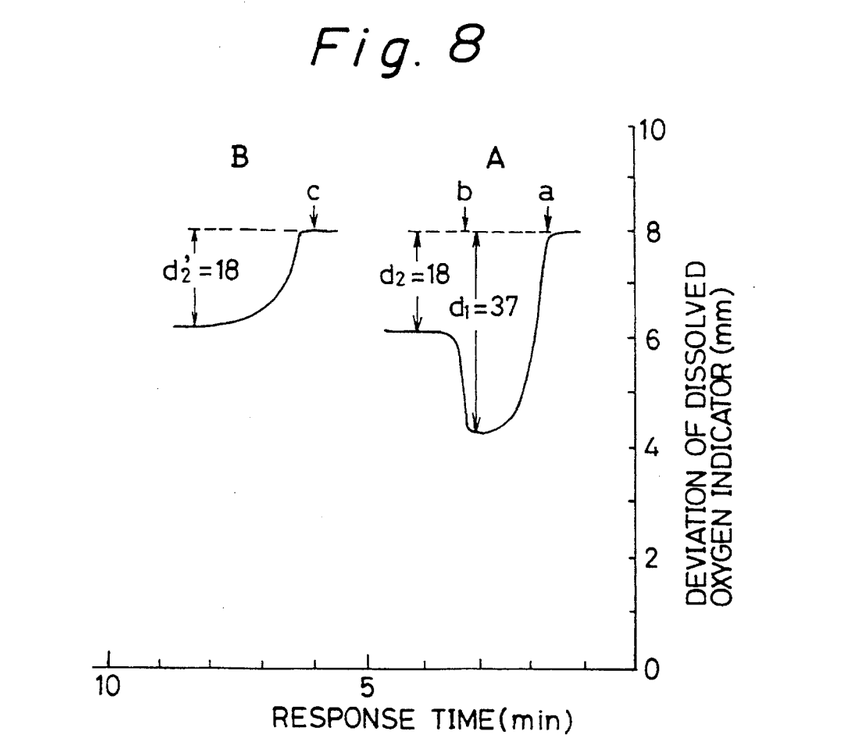
FIG. 8 is a DO response curve graph for showing an effect caused by adding a large amount of catalase.

Curve A in FIG. 8 shows an effect caused by addition of catalase in a model experiment. Histamine oxidase was added to the histamine standard solution at the point "a". When DO uptake finished at the point "b", 20 μl of catalase solution (Oriental Denki, used for hydrogen peroxide measuring device, 5000 U/ml) was added. The catalase solution begun immediately to decompose $H_2O_2$ produced by action of histamine oxidase. A DO response shows clearly that a half of the initial oxygen uptake can be yielded. Curve B of FIG. 8 is a response curve DO in the case where histamine oxidase and catalase were previously mixed into the same substrate. As the result of synthetic reaction of the aforementioned formulas (2) and (3), a relation was obtained in which a half of oxygen uptake caused by a single use of histamine oxidase i.e. 1 mole of oxygen to 2 moles of histamine was obtained. In this reaction system, DO does not increase since no $H_2O_2$ remains.

This method is very useful for a sample including a large amount of catalase. By making use of the fact that oxygen uptake for the substrate is reduced in half, the method has an advantage that a dynamic range of determination is enlarged twice as much when the method is employed for a sample of high concentration of histamine.

FIG. 3 illustrates a graph showing a proportional relationship of 1:1 between histamine concentration ($C_{Hm}$) and oxygen uptake. FIG. 4 illustrates a graph showing a used amount of enzyme suspension and uptake amount of oxygen. It shows that a ratio of histamine to oxygen uptake becomes 1:1 by sufficient addition of enzyme.

IX. Example of Histamine Determination in Fishes

A commercially available red meat fish was stored at a refrigerator or an isothermal device at a temperature of 30° C. Then, a production of histamine in accordance with decrease of freshness was measured in the aforementioned method. A preparation method of the sample solution is as follows.

1) 15 ml of TCA (10%) is added into 10 g of sample.
2) Homogenizing
3) One or two drops of methyl red are added to the homogenized mixture, neutralized by 10 N KOH, filtered, and adjusted to be at pH 8 to 11 using pH meter.
4) A filtered liquid is filled up in a volumetric flask of 50 ml to obtained a sample solution.

This sample solution is also used for measuring K value.

For the measurement, air saturated system P.B. is filled in a reaction cell, at first. After 10 to 20 μl of sample solution is injected in the reaction cell, 15 μl of enzymatic solution is injected. If a DO decrease is not confirmed due to the small quantity of the histamine then the sample amount is increased to 100 μl. For a sample containing an even smaller amount of histamine, the air saturated sample solution is diluted 2–4 times with P.B. and loaded in the reaction cell and determination is carried out. (without using P.B.).

Method of calculation:

an amount of histamine per 50 ml of sample solution is calculated. This amount of histamine corresponds to 10 g of sample. So, the amount of histamine per 100 g of sample is calculated by multiplying it by ten.

A formula weight of histamine is 111. Therefore, uptake $DO$ (mM) × 5.55 (mg/l/mM)

By the above calculation, the value of mg of histamine per 50 ml of sample solution is calculated. Therefore, a content of histamine per 100 g of sample can be easily calculated by multiplying by coefficient of 55.5. Table 2 shows results of determination of content of histamine in mackerel, tuna, and horse mackerel.

Determination values in Table 2 show histamine mg/100 g specimen.

TABLE 2

| Sample | Storage Condition | | |
|---|---|---|---|
| | 5° C., 7 days | 30° C., 1 days | 30° C., 2 days |
| Mackerel (raw) | 51.2 | 2.68 | 126. |
| Tuna (raw) | 11.6 | 0.15 | 51.7 |
| Horse Mackerel (semi-dried) | 0.33 (measured just after purchased) | | |

Figure 9:
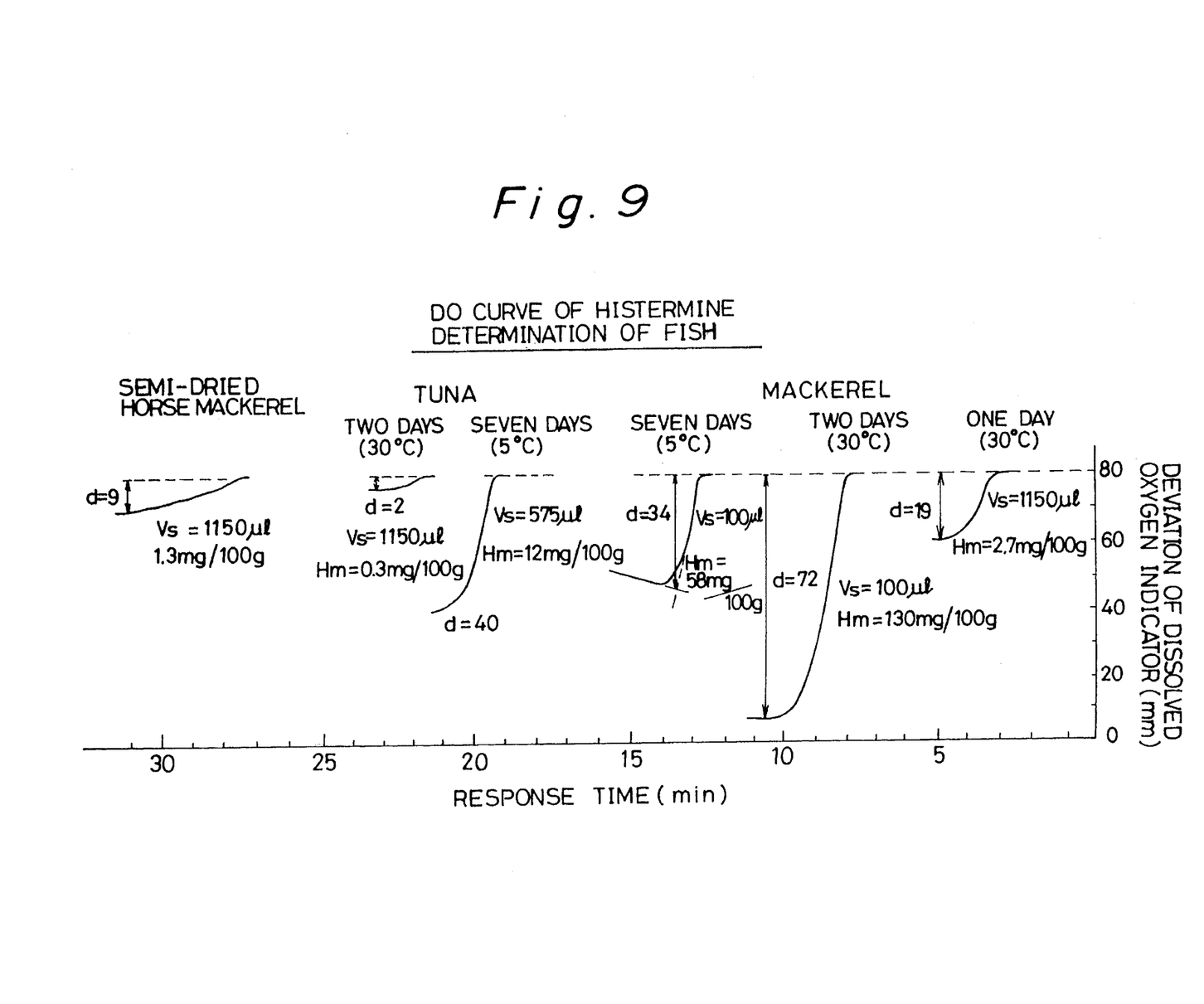
FIG. 9 is a DO response curve graph of histamine determination in fishes of various species according to the present invention.

As to fish extract liquid, an enzymatic reaction progresses smoothly in the absolutely same manner as that of the pure histamine solution, as clearly seen from DO curve in FIG. 9. Determination of histamine can be carried out for an extremely short period of about 1.5 minutes.

It is conventionally known that fishes such as mackerel, tuna or the like belonging to a mackerel family have a remarkable tendency to produce histamine. The results obtained by the embodiments prove the above.

X. Addition and Recovery Test of Histamine to Tuna Sample.

Table 3 shows determination result of very good recovery of histamine added to canned tuna extract.

The terms in Table 3 are as follows:

Background; histamine amount in extract liquid of tuna

Added ; adding amount of pure histamine dihydrochloride soln.

Found ; analysis value in Reaction Cell

Recovery ; recovering amount of histamine addition for tuna is shown by the following equation:

Recovery(%)=(Found-Background)/added*100.

TABLE 3

| Sample | Background (μM) | Added (μM) | Found (μM) | Recovery (%) |
|---|---|---|---|---|
| HI | 10.7 | 36.1 | 45.7 | 97 |
| | | 72.2 | 83.7 | 101 |
| | | 108 | 122 | 102 |
| | | 144 | 158 | 102 |
| LAB | 30.8 | 36.1 | 69.2 | 106 |
| | | 72.2 | 108 | 106 |
| | | 108 | 143 | 103 |
| H2 | 13.4 | 36.1 | 52.3 | 107 |
| | | 72.2 | 93.5 | 111 |
| | | 108 | 128 | 106 |
| | | 144 | 167 | 107 |

XI. Correlation between AOAC method and DO sensor method 1. Comparative determination on canned tuna extracted by 10% TCA solution.

Table 4 shows determining results of histamine using AOAC method and DO sensor method on the same 10% TCA extract of canned tuna.

TABLE 4

| Sample | Histamine determined (mg %) | | |
|---|---|---|---|
| | AOAC | DO Sensor | Difference |
| LAB220Z (1) | 0.67 | 0.89 | −0.22 |

TABLE 4-continued

| Sample | Histamine determined (mg %) | | |
|---|---|---|---|
| | AOAC | DO Sensor | Difference |
| LAB220Z (2) | 0.56 | 0.69 | −0.13 |
| H1 (1) | 9.88 | 10.24 | −0.36 |
| H1 (2) | 9.69 | 12.03 | −2.34 |
| H2 (1) | 46.23 | 46.09 | 0.14 |
| H2 (2) | 47.45 | 45.58 | 1.87 |

2. Comparative determination on canned tuna extracted by heated 0.1M, pH 8.0, P.B.

Table 5 shows the same experimental phosphate buffer extract of canned tuna.

TABLE 5

| Sample | Histamine determined (mg %) | | |
|---|---|---|---|
| | AOAC | DO Sensor | Difference |
| LAB220Z (1) | 0.67 | 0.98 | −0.31 |
| LAB220Z (2) | 0.56 | 1.23 | −0.67 |
| H1 (1) | 9.88 | 9.56 | 0.32 |
| H1 (2) | 9.69 | 9.29 | 0.4 |
| H2 (1) | 46.23 | 46.09 | 0.14 |
| H2 (2) | 47.45 | 44.66 | 2.79 |

In both cases, very high correlation (r=0.999) between AOAC method and DO sensor method was confirmed.

3. Comparative determination on Raw Tuna and Mackerel extracted by 10% TCA

Figure 10:
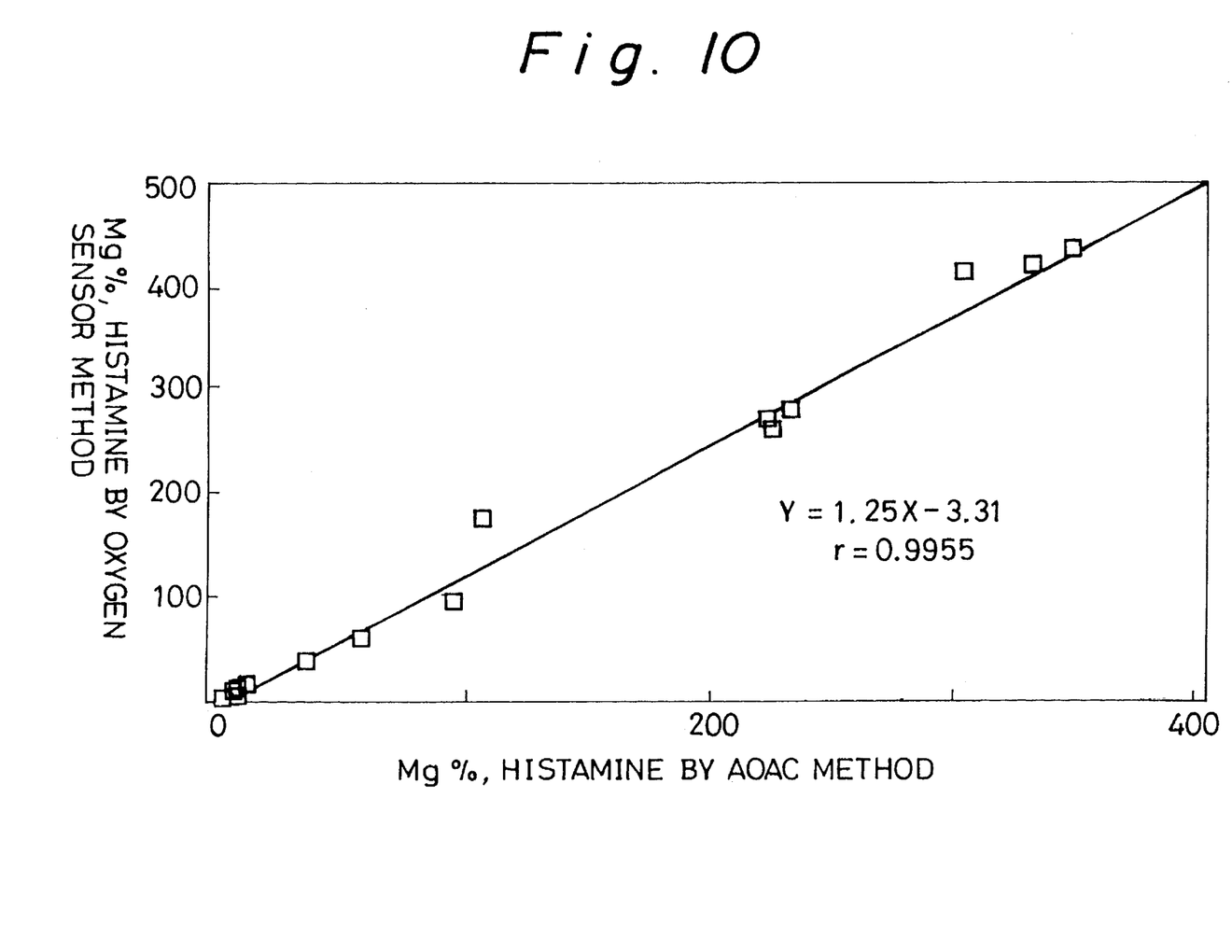
FIG. 10 is a comparative determination on Raw Tuna and Mackerel extracted by 10% TCA.

FIG. 10 shows results of comparative determination between AOAC method and DO sensor method on raw fishes extract. High correlation coefficient (r=0.9955) was given.

According to these results, the present method clearly explains to have very good reliability. Further, it is turned out that the present histamine determining method is simpler and twice rapid than the conventional method.

It is generally said that a crisis of poisoning occurs when a fish containing not less than 100 mg/100 g of histamine is eaten. In the method according to the present invention, an extremely small amount of histamine in the vicinity of 0.1 mg/100 g can be detected to be determined by adjusting an extract liquid into the reaction cell, while a large amount of histamine of order of 100 mg can be determined. Therefore, this method is useful for detection of initial decomposition of mackerel and tuna which were examined by NAGAYAMA et al. [EISEI KAGAKU: Vol. 31, 362 to 372 (1985)]. Further, It is recognized that this method can be used for determination of histamine in blood and biological liquid.

Many widely different embodiments of the present invention may be constructed without departing from the spirit and scope of the present invention. It should be understood that the present invention is not limited to the specific embodiments described in the specification, except as defined in the appended claims.

What is claimed is:

1. In a method of determining the histamine concentration in a sample by determining a decrease in dissolved oxygen (DO), the improvement comprising the steps of:

adding a solution of an enzymatic reagent having histamine oxidase activity into an examination liquid containing said sample;

detecting a sensor output signal $d_o$ proportional to DO saturated concentration $C_{O2}$ of said examination liquid by using a DO analyzer having a reaction cell provided with a DO electrode;

measuring a decrease d of sensor output resulted from adding said enzymatic reagent, said decrease d having been obtained by continuing the DO recording until DO decrease stops; and determining concentration of histamine ($C_{Hm}$) in the reaction cell by the following formula:

$$C_{Hm} = C_{O_2} \times \frac{d}{d_0} \text{ (mM)}$$

2. In a method according to claim 1, the improvement additionally comprising carrying out the determining step while preventing an inhibitory reaction of catalase by the presence of sodium azide in said examination liquid.

3. In a method according to claim 2, the improvement additionally comprising carrying out the determining step while decomposing $H_2O_2$ by adding a large amount of catalase into the examination liquid and erasing an influence that results from mixing catalase.

4. The method according to claim 2, wherein an amount of said sodium azide is about 3 mM.

5. The method according to claim 1, wherein the pH of said examination liquid is in the range from 7 to 11, and the temperature of said examination liquid is in the range of 20° to 40° C.

6. The method according to claim 5, wherein the pH and temperature of said examination are in the range from 8 to 9 and at 37° C., respectively.

7. The method according to claim 1, wherein said enzymatic reagent is a Cu-containing fungal amine oxidase.

8. The method according to claim 7, wherein said Cu-containing fungal amine oxidase is about $10^5$ Unit/ml.

9. In a method according to claim 8, wherein said Cu-containing fungal amine oxidase is extracting the Cu-containing fungal amine oxidase from a cell mass belonging to *Aspergillus niger* cultured in a culture medium including amine as a nitrogen source;

purifying the extracted enzyme by using ammonium sulfate salting-out, dialysis, DEAE-column chromatography or the like;

further purifying the once purified enzyme up to a high purity by an affinity chromatography or a hydroxyapatite chromatography;

concentrating the further purified enzyme through dialysis tube by using glycerin; and suspending the concentrated enzyme in an ammonium sulfate solution.

* * * * *